US006406688B1

(12) United States Patent
White et al.

(10) Patent No.: US 6,406,688 B1
(45) Date of Patent: Jun. 18, 2002

(54) METHOD OF TREATING SEPSIS AND ARDS WITH CHEMOKINE β-4

(75) Inventors: John Richard White, Coatesville; Louis Martin Pelus, Richboro, both of PA (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/496,273

(22) Filed: Feb. 1, 2000

Related U.S. Application Data

(62) Division of application No. 08/852,212, filed on May 6, 1997, now Pat. No. 6,290,948.
(60) Provisional application No. 60/017,871, filed on May 14, 1996.

(51) Int. Cl.$^7$ ................................................ A61K 38/19
(52) U.S. Cl. .............................. 424/85.1; 514/2; 514/8; 514/12
(58) Field of Search ............................. 424/85.1; 514/2, 514/8, 12

(56) References Cited

U.S. PATENT DOCUMENTS

| | | |
|---|---|---|
| 4,897,338 A | 1/1990 | Johnson et al. |
| 5,278,287 A | 1/1994 | Rollins et al. |
| 5,306,709 A | 4/1994 | Gewirtz et al. |
| 5,346,686 A | 9/1994 | Lyle et al. |
| 5,413,778 A | 5/1995 | Kunkel et al. |
| 5,474,983 A | 12/1995 | Kuna et al. |

FOREIGN PATENT DOCUMENTS

| | | |
|---|---|---|
| EP | 0538 030 2 | 4/1993 |
| JP | 07089866 | 4/1995 |
| WO | WO90/06321 | 6/1990 |
| WO | WO91/04274 | 4/1991 |
| WO | WO91/12815 | 9/1991 |
| WO | WO92/05198 | 4/1992 |
| WO | WO92/20372 | 11/1992 |
| WO | WO95/17092 | 6/1995 |
| WO | WO95/31468 | 11/1995 |
| WO | WO96/05856 | 2/1996 |
| WO | WO96/06169 | 2/1996 |
| WO | WO96/09062 | 3/1996 |
| WO | WO96/16979 | 6/1996 |
| WO | WO96/39520 | 12/1996 |
| WO | WO96/39521 | 12/1996 |
| WO | WO96/39522 | 12/1996 |
| WO | WO97/31098 | 3/1997 |
| WO | WO97/15594 | 5/1997 |
| WO | WO97/15595 | 5/1997 |
| WO | WO 97/19173 | 5/1997 |
| WO | WO 97/35027 | 9/1997 |
| WO | WO97/35982 | 10/1997 |
| WO | WO 97/41831 | 11/1997 |
| WO | WO/98/11226 | 3/1998 |
| WO | WO98/14573 | 4/1998 |
| WO | WO98/09171 | 5/1998 |

OTHER PUBLICATIONS

Geneseq Accession No: R93087 (Aug. 27, 1996).
Geneseq Accession No: W22670 (Mar. 19, 1998).
Geneseq Accession No: W30191 (May 21, 1998).
Geneseq Accession No: W56087 (Aug. 17, 1998).
Geneseq Accession No: W56690 (Jul. 23, 1998).
Geneseq Accession No: W57475 (Sep. 7, 1998).
Geneseq Accession No: W44398 (Jun. 11, 1998.
Geneseq Accession No: W61279 (Sep. 24, 1998).
Geneseq Accession No: T90880 (May 21, 1998).
Geneseq Accession No: V28591 (Aug. 17, 1998).
Geneseq Accession No: W17660 (Dec. 16, 1997).
Geneseq Accession No: R95690 (Dec. 20, 1996).
Geneseq Accession No: T90883 (May 21, 1998).
GenBank Accession No: U77035 (Jan. 23, 1997).
GenBank Accession No: D86955 (Mar. 6, 1997).
GenBank Accession No: U64197 (Jun. 25, 1997).
GenBank Accession No: I35613 (Feb. 26, 1997).
GenBank Accession No: U46767 (Dec. 14, 1996).
GenBank Accession No: X98306 (Jul. 20, 1998).
Hieshima, K., et al., J. Immunol., vol. 159:1140–9 (1997).
Kodelja, V., et al., The J. Immunology, vol. 160:1411–1418 (1998).
Patel, V. P., et al., J. Exp. Med., vol. 185:1163–1172 (1997).
Taub, D. D. et al., Therapeutic Immunology, vol. 1:229–246 (1994).
George et al., Macromolecular Sequencing & Synthesis, Ch. 12:127–149 (1988).
Berger, M. S. et al., Clinical Research, vol. 42:305A (1994).
Uguccioni, M. et al., J. Exp. Med., vol. 183:2379–2384 (1996).
Craddock et al., Blood, vol. 90:4779–4788 (1997).
Liu et al., Blood, vol. 90:2522–2528 (1997).
Laterveer et al., Blood, vol. 87:781–788 (1996).
Laterveer et al., Exp. Hematology, vol. 24:1387–1393 (1996).
Blum, S. et al., DNA and Cell Biology, vol. 9:589–602 (1990).
Obaru, K., et al., J. Biochem., vol. 99:885–894 (1986).
Derynck, R., et al., Biochemestry, vol. 29:10225–10233 (1990).
Sudo, K. et al., Genomics, vol. 24:276–276 (1994).
Lukacs, N. W., et al., J. Exp. Med., vol. 177:1551–1559 (1993).
Jose, P. J. et al., J. Exp. Med. vol. 179:881–887 (1994).
Kuna, P. et al., The J. of Exp. Med. vol. 175:489–493 (1992).
Matsushima, K. et al., The J. of Exp. Med. vol. 169:1485–1490 (1989).

(List continued on next page.)

Primary Examiner—Prema Mertz
(74) Attorney, Agent, or Firm—Sterne, Kessler, Goldstein & Fox P.L.L.C.

(57) ABSTRACT

The invention relates to the method of preventing and treating sepsis and ARDS using chemokine β-4 or a biologically active fragment thereof, alone or in conjunction with an anti-infective agent.

10 Claims, No Drawings

OTHER PUBLICATIONS

Schall, T. J. et al., Cytokine, vol. 3:165–183 (1991).
Clements J. M., et al., Cytokine, vol. 4:72–82 (1992).
Zipfel, P. F., et al., The J. of Immunology, vol. 142: 1582–1590 (1989).
Graham, G. J. et al., Development Biology, vol. 151:377–381 (1992).
Bioschoff, S. C., et al., J. Exp. Med., vol. 175:1271–1275 (1992).
Lerner, R. A. et al., Nature, vol. 299 (1982).
Nakao, M. et al., Molecular and Cellular Biology, vol. 10:3646–3658 (1990).
Kwon, Y. S. et al., Proc. Natl. Acad. Sci., vol. 86:1963–1967 (1989).
Widmer, U. et al., J. Immunology, vol. 150:4996–5012 (1993).
Schall, T. et al., Eur. J. Imm. vol. 22:1477–1481 (1992).
Furuta, R. et al., J. Biochem., vol. 106:436–441 (1989).
Brown, et al., J. Immunology, vol. 142:679–687 (1989).
Kurdowska, A. et al., Cytokine, vol. 6:124–134 (1994).
International Search Report, EP 97 30 3204 (Jan. 23, 1998).
Berkow, R. et al., eds., *The Merck Manual,* 16$^{th}$ Edition, Merck & Co., Inc., Rahway, N.J., p. 643 (1992).

METHOD OF TREATING SEPSIS AND ARDS WITH CHEMOKINE β-4

RELATED APPLICATION

This application is a divisional of U.S. application Ser. No. 08/852,212, filed May 6, 1997, now U.S. Pat. No. 6,290,948, which claims priority under 35 U.S.C. §119(e) to Provisional Application No. 60/017,871, filed May 14, 1996.

FIELD OF INVENTION

This invention relates to the method of preventing and treating sepsis and adult respiratory distress syndrome using certain chemokines or biologically active fragments thereof alone or in conjunction with an anti-infective agent or hematopoietic maturing agent.

BACKGROUND OF INVENTION

Sepsis, as used herein, is broadly defined to mean situations when the invasion of a host by a microbial agent is associated with the clinical manifestations of infection including but not limited to:

(1) temperature >38° C. or <36° C.; (2) heart rate >90 beats per minute; (3) respiratory rate >20 breaths per minute or $PaCO_2$<32 mm Hg; (4) white blood cell count >12,000/cu mm, <4,000/cu mm, or >10% immature (band) forms; (5) organ dysfunction, hypoperfusion, or hypotension. Hypoperfusion and perfusion abnormalities may include, but are not limited to lactic acidosis, oliguria, or an acute alteration in mental states. (Chest 1992; 101: 1644–1566).

Sepsis can occur in hospitalized patients having underlying diseases or conditions that render them susceptible to bloodstream invasion or in burn, trama or surgical patents. In many cases of sepsis, the predominant pathogen is *Escherichia coli*, followed by other Gram-negative bacteria such as the Klebsiella-Enterobacter-Serratia group and then Pseudomonas. Although comprising a somewhat smaller percentage of infection, Gram-positive microbes such as Staphylococcus and systemic viral and fungal infections are included by the term sepsis as used herein. The genitourinary tract is the most common site of infection, the gastrointestinal tract and respiratory tract being the next most frequent sources of sepsis. Other common foci are wound, burn, and pelvic infections and infected intravenous catheters.

A serious consequence of bacterial sepsis often is septic shock. Septic shock is characterized by inadequate tissue perfusion, leading to insufficient oxygen supply to tissues, hypotension and olgiuria.

Septic shock occurs because bacterial products react with cells and components of the coagulation, complement, fibrinolytic and bradykinin systems to release proteases which injure cells and alter blood flow, especially in the capillaries.

Microorganisms frequently activate the classical complement pathway, and endotoxin activates the alternative pathway. Complement activation, leukotriene generation and the direct effects of bacterial products on neutrophils lead to accumulation of these inflammatory cells in the lungs, release of their proteolytic enzymes and toxic oxygen radicals which damage the pulmonary endothelium and initiate the adult respiratory distress syndrome ("ARDS"). ARDS is a major cause of death in patients with septic shock and is characterized by pulmonary congestion, granulocyte aggregation, haemorrhage and capillary thrombi.

Septic shock is a major cause of death in intensive care units. There are an estimated 200,000 cases per year of septic shock in the United States, and despite advances in technology (i.e., respiratory support) and antibiotic therapy, the mortality rate for septic shock remains in excess of 40%. In fact, mortality for established septic shock has decreased very little since the comprehensive description by Waisbren (*Arch. Intern. Med.* 88:467–488 (1951)). Although effective antibiotics are available, and there is an increased awareness of the septic shock syndrome, the incidence of septic shock over the last several decades has actually increased. With the appreciation that antimicrobial agents have failed to completely abrogate septic mortality, it is clear that other agents must be developed to be used alone or in conjunction with antimicrobials in order to rectify the deficiencies of current established therapy.

BRIEF DESCRIPTION OF THE INVENTION

This invention relates to a method of preventing or treating sepsis and ARDS comprising administering to an animal, including humans, in need thereof an effective amount of chemokine protein or biologically active fragments thereof.

This invention further relates to a method of preventing or treating sepsis and ARDS comprising administering to an animal (including humans) in need thereof an effective amount of chemokine protein or biologically active fragments thereof, either before, in conjunction with or after an anti-infective agent.

DETAILED DESCRIPTION OF THE INVENTION

It is the object of this invention to provide a new method of treatment of sepsis and ARDS comprising administering to an animal in need thereof, including humans, an effective amount of chemokine protein or biologically active fragments thereof, alone or in combination with other anti-infective agents. As used herein the term "chemokine" means Chemokine Beta-4 (SEQ ID NOs: 1 and 2). The initial 24 amino acids represent the deduced leader sequence of Chemokine Beta-4 such that the putative mature polypeptide comprises 72 amino acids.

TABLE 1

Chemokine Patent Applications

| Gene Name | Date Filed | Application Number |
|---|---|---|
| Macrophage Inflammatory Protein-Gamma | Dec-22-93 | 08/173,209 |
| Macrophage Inflammatory Protein-3 and -4 | Mar-8-84 | WO95/17092 |
| Macrophage Migration Inhibitory Factor-3 | May-16-94 | WO95/31468 |
| Human Chemokine Beta-9 | Jun-6-95 | WO96/06169 |
| Human Chemokine Polypeptides | Aug-23-94 | WO96/05856 |
| Human Chemokine Beta-11 and Human Chemokine Alpha 1 | Feb-8-95 | US95/01780 |
| Human Chemokine Beta-13 | Jun-5-95 | 08/464,594 |
| Human Chemokine Beta-12 | Jun-6-95 | 08/468,541 |
| Chemokine Alpha-2 | Mar-19-96 | 60/013,653 |
| Chemokine Alpha-3 | Mar-18-96 | US96/03686 |
| Novel Chemokine for Mobilizing Stem Cells | Sep-29-95 | 60/006,051 |
| Short Form Chemokine Beta-8 | Oct-24-95 | 60/004,517 |

This invention further relates to a method of preventing sepsis and ARDS comprising administering to an animal in need thereof an effective amount of modified chemokine protein or biologically active fragments thereof alone or in combination with other anti-infective agents.

Known anti-infective agents include, without limitation, anti-microbial agents routinely used for the treatment of sepsis such as amino-glycosides (such as amikacin, tobramycin, netilmicin, and gentamicin), cephalosporins such as ceftazidime, related beta-lactam agents such as maxalactam, carbopenems such as imipenem, monobactam agents such as aztreonam; ampicillin and broad-spectrum penicillins, (e.g., penicillinase-resistant penicillins, ureidopenicillins or antipseudomonal penicillin or Augmentin) that are active against *P. aeruginosa*, Enterobacter species, indole-positive Proteus species, and Serratia. Also included within the definition of anti-infective agents are antifungal agents, amphotericin and the like as well as anti-viral agents such as famvir and acyclovir.

The compound is useful in the treatment and prevention of sepsis and ARDS in humans and other animals such as dairy cattle, horses, calves or poultry.

Chemokine protein or biologically active fragments of Chemokine Beta-4 have been described. The use of chemokine protein or biologically active fragments thereof for the prevention and treatment of sepsis has not been reported. It has now been discovered that chemokine protein or biologically active fragments thereof significantly increases the survival of animals challenged with lethal sepsis causing organisms. Treatment with the compound of this invention, alone or in combination with an anti-infective agent prior to contemplated thoracic or abdominal surgery would be useful in reducing the likelihood of post-operative sepsis. It may also be used post-operatively for the treatment of sepsis and ARDS caused by a variety of reasons as outlined previously.

To effectively treat a human or other animal chemokine protein or biologically active fragments thereof may be amstered by injection in the dose range of about 10 fg/kg to about 100 mg/kg/dose, preferably between about 1 and 50 mg/kg/dose, or orally in the dose range of about 10 fg/kg to about 100 mg/kg body weight per dose, preferably between about 1 and 50 mg/kg body weight; if administered by infusion or similar techniques, the dose may be in the range of about 10 fg/kgto about 100 mg/kg/dose, preferably between about 1 and 50 mg/kg/dose; if administered subcutaneously the dose may be in the range of about 10 fg/kg to about 100 mg/kg/dose, preferably between about 1 and 50 mg/kg/dose.

Depending on the patient's condition, the compounds of this invention can be administered for prophylactic and/or therapeutic treatments. In therapeutic application, the compound is administered to a patient already suffering from a disease in an amount sufficient to cure or at least partially arrest the disease and its complications. It may be given at any time after surgery, preferably prior to 24 hours after surgery. In prophylactic applications, a composition containing chemokine protein or biologically active fragments thereof, is administered to a patient not already in a disease state to enhance the patient's resistance. It may be given one day or one week prior to surgery, preferably one to two days prior to surgery. It may be administered parenterally or orally.

Single or multiple administrations of the compounds can be carried out with dose levels and pattern being selected by the treating physician. In any event, a quantity of the compounds of the invention sufficient to effectively treat the patient should be administered.

The compounds of this invention, may also be administered in conjunction with a conventional anti-infective as disclosed herein above, such as gentamicin, augmentin or ceftazidime. The particular anti-infective chosen should be one to which the infective organism is susceptible and is selected or modified during therapy as the infecting microorganism is more particularly identified.

Additionally, various adjunctive agents in the treatment of septic shock also may be useful in combination with the components of this invention. They include sympathomimetic amines (vasopressors) such as norepinephrine, epinephrine, isoproterenol, dopamine, and dobutamine; anti-inflammatory agents such as methylprednisolone anti-inflammatory agents such as indomethacin and phenylbutazone; and corticosteroids such as betamethasone, hydrocortisone, methylprednisolone, or dexamethasone; anti-coagulants such as heparin, anti-thrombin III or coumarin type drugs for certain conditions and schedules; diuretics such as furosemide or ethacrynic acid; and antagonist of opiates and beta-endorphins such as naloxone; an antagonist of tumor necrosis factor or of interleukin-1; phenothiazines; anti-histamines; glucagon; α-adrenergic blocking agents, vasodilators; plasma expanders; packed red blood cells; platelets; cryoprecipitates; fresh frozen plasma; bacterial permeability protein; clindamycin; and antibodies to (lipid A), the J5 mutant of *E. coli* or to endotoxin core glycolipids. Methods for preparing such antibodies are described widely in the literature.

One of the most important aspects in the treatment of the clinical septic shock syndrome is its apparently intractable resistance to the effects of a variety of highly potent antimicrobial agents. Despite the development of newer antimicrobial agents, the overall incidence of clinical sepsis has increased, and mortality remains unacceptably high, often approaching 60% of diagnosed patients. The discovery of the increased survival with the treatment of chemokine protein or biologically active fragments thereof both prophylactically and after infection provides a new and useful therapy of sepsis and ARDS.

The compounds of this invention, may also be administered in conjunction with hematopoietic maturation agents, such as G-CSF, F1t3, M-CSF or GM-CSF. These compounds affect the mobilization of the chemokines of the invention and are believed to enhance the anti-sepsis and anti-ARDS efficacy of chemokines.

The biological activity of chemokine protein or biologically active fragments thereof are demonstrated by the following assays:

Rats. Male Fischer 344 rats obtained from Taconic farms weighing 200 to 250 g. are utilized. The rats are housed 2 per cage in standard plastic caging and fed lab chow and water ad libitum.

Chemokine protein or biologically active fragments thereof, is prepared in *E. coli* by the method given in Example 5. The compound is dissolved in DPBS containing 0.5% heat inactivated autologous normal rat serum. The animals are dosed intraperitoneally with chemokine 24 hours and 2 hours before infection. Control animals are dosed with dilution buffer on the same schedule. Starting two hours after infection the rats are treated twice daily with subcutaneous gentamicin.

*E coli*. A clinical isolate of *E. coli* isolated from sputum is utilized. The organisms are tested for antibiotic sensitivity by the disc-agar diffusion technique and found to be sensitive to gentamicin, ampicillin, cephalothin, chloramphenicol, kanamycin, tetracycline, trimethoprin/sulfamethoxazole and resistant to penicillin G, erythromycin, and vancomycin. The organism is animal passed in mice and subsequently recovered and plated onto MacConkey's agar. The reisolated organisms are grown overnight in brain-heart infusion broth, and then stored frozen at −70° C. To inoculate the fibrin clot, organisms from thawed stocks are inoculated into brainheart infusion broth and incubated overnight on a rotary shaker (120 rpm) at 37° C. The E. coli is harvested by centrifugation, washed 3× and finally resuspended in normal saline. The number of organisms is quantified by turbidimentry, and the concentration adjusted with normal saline. All inoculum sizes are based on viable counts determined by scoring colony forming units on MacConkeys agar.

Fibrin Clot. The E. coli infected fibrin clots are made from a 1% solution of bovine fibrinogen (Type 1-S, Sigma) in sterile saline. The clot is formed by adding sequentially human thrombin (Hanna Pharma.) bacteria, and fibrinogen solution to 24 well plastic plates. Bacterial numbers of 2.0 to $3.0 \times 10^9$ are used in inoculate the fibrin clots. The resulting mixture is then incubated at room temperature for 30 minutes before implantation.

Animal Model. The rats are anethetized with ketamine/xylazine (40 mg/kg/5 mg/kg) then the abdominal surfaced is shaved and a midline laporatomy performed. Bacterial peritonitis is induced by implanting a fibrin-thrombin clot containing E. coli into the abdominal cavity. After implantation the muscle layers are closed with 4-0 silk suture, and the wound closed with surgical staples. The animals are closely observed, any animals obviously moribound are euthanized.

Gentamicin. Rats are treated subcutaneously with gentamicin sulfate (Elkins-Sinn, N.J.) 5 mg/kg twice a day for five days.

Statistics. All continuously variable data are expressed as the percent survival from several pooled studies. The Fisher's Exact test is used to determine the statistical significance of the differences between the survival rates at 14 days. The differences between the groups are considered statistically significant at $p<0.05$.

EXAMPLE 1
Prophylactically Administered Chemokine.

Chemokine proteins may be prepared using known methods for protein purification or as described for Chemokine Beta-4.

The animals are dosed intraperitoneally with chemokine at doses of 10, 100 and 1,000 fg/kg, and 10 and 100 mg/kg 24 hours and 2 hours before infection. Control animals are dosed with dilution buffer on the same schedule. Starting two hours after infection the rats are treated twice daily with subcutaneous gentamicin. On day 0 the rats are implanted with an E. coli containing fibrin-thrombin clot Starting two hours after infection the rats are treated with gentamicin twice daily. The rats prophylactically treated with chemokine at 33 or 100 fg/kg followed by gentamicin treatment demonstrated significantly improved survival rates over the diluent treated control rat receiving gentamicin therapy alone.

EXAMPLE 2
Theraputically Administered Chemokine.

On day 0 the rats are implanted with an E. coli containing fibrin-thrombin clot. The animals are dosed intraperitoneally with chemokine at doses of 10, 100 and 1,000 fg/kg, and 10 and 100 mg/kg as a single injection 2 hours after infection. Control animals are dosed with dilution buffer on the same schedule. Starting two hours after infection the rats are treated twice daily with subcutaneous gentamicin. The rats theraputically treated with chemokine at 100 or 333 fg/kg followed by gentamicin treatment are assessed for improved survival rates over the diluent treated control rat receiving gentamicin therapy alone.

EXAMPLE 3
Therapeutically Administered Chemokine in S. Aureus Sepsis.

On day 0 the rats are implanted with a S. aureus containing fibrin-thrombin clot. The animals are dosed intraperitoneally with chemokine at doses of 10, 100 and 1,000 fg/kg, and 10 and 100 mg/kg as a single injection 2 hours after infection. Control animals are dosed with dilution buffer on the same schedule. Starting two hours after infection the rats are treated twice daily with subcutaneous gentamicin. The rats theraputically treated with chemokine followed by gentamicin treatment are assessed for improved survival rates over the diluent treated control rat receiving gentamicin therapy alone.

What is claimed is:

1. A method of treating sepsis and adult respiratory distress syndrome (ARDS) comprising administering to an animal in need thereof an effective amount of a polypeptide selected from the group consisting of:
   (a) a polypeptide comprising the amino acid sequence in SEQ ID NO:2;
   (b) a polypeptide comprising amino acids 25 to 96 in SEQ ID NO:2;
   (c) a polypeptide comprising a portion of the amino acid sequence in SEQ ID NO:2, wherein said portion is chemotactic for leukocytes.

2. The method of claim 1, wherein said polypeptide is (a).
3. The method of claim 1, wherein said polypeptide is (b).
4. The method of claim 1, wherein said polypeptide is (c).
5. The method of claim 1, wherein the effective amount is from about 1 to about 100 mg/kg/dose.
6. The method of claim 1, wherein said polypeptide is administered parenterally.
7. The method of claim 1, wherein said polypeptide is administered in conjunction with an anti-infective agent.
8. The method of claim 7, wherein said anti-infective agent is selected from the group consisting of: gentamicin, augmentin, and ceftazidime.
9. The method of claim 1, wherein said polypeptide is administered 1 to 2 days prior to surgery.
10. The method of claim 1, wherein said animal is a human.

* * * * *

SEQUENCE LISTING

```
<160> NUMBER OF SEQ ID NOS: 2

<210> SEQ ID NO 1
<211> LENGTH: 291
<212> TYPE: DNA
<213> ORGANISM: Homo sapiens
<220> FEATURE:
<221> NAME/KEY: CDS
<222> LOCATION: (1)..(288)
<221> NAME/KEY: misc_feature
<223> OTHER INFORMATION: Chemokine Beta-4

<400> SEQUENCE: 1 atg tgc tgt acc aag agt ttg ctc ctg gct g ct ttg atg tca gtg ctg      48
Met Cys Cys Thr Lys Ser Leu Leu Leu Ala A la Leu Met Ser Val Leu
1               5                   10                  15 cta ctc cac ctc tgc ggc gaa tca gaa gca g ca agc aac ttt gac tgc      96
Leu Leu His Leu Cys Gly Glu Ser Glu Ala A la Ser Asn Phe Asp Cys
            20                  25                  30 tgt ctt gga tac aca gac cgt att ctt cat c ct aaa ttt att gtg ggc     144
```

-continued

```
Cys Leu Gly Tyr Thr Asp Arg Ile Leu His Pro Lys Phe Ile Val Gly
            35                  40                  45 ttc aca cgg cag ctg gcc aat gaa ggc tgt gac atc aat gct atc atc        192
Phe Thr Arg Gln Leu Ala Asn Glu Gly Cys Asp Ile Asn Ala Ile Ile
    50                  55                  60 ttt cac aca aag aaa aag ttg tct gtg tgc gca aat cca aaa cag act        240
Phe His Thr Lys Lys Lys Leu Ser Val Cys Ala Asn Pro Lys Gln Thr
65                  70                  75                  80 tgg gtg aaa tat att gtg cgt ctc ctc agt aaa aaa gtc aag aac atg        288
Trp Val Lys Tyr Ile Val Arg Leu Leu Ser Lys Lys Val Lys Asn Met
                85                  90                  95 taa                                                                     291
```

<210> SEQ ID NO 2
<211> LENGTH: 96
<212> TYPE: PRT
<213> ORGANISM: Homo sapiens
<220> FEATURE:
<221> NAME/KEY: misc_feature
<223> OTHER INFORMATION: Chemokine Beta-4

<400> SEQUENCE: 2

```
Met Cys Cys Thr Lys Ser Leu Leu Leu Ala Ala Leu Met Ser Val Leu
1               5                   10                  15

Leu Leu His Leu Cys Gly Glu Ser Glu Ala Ala Ser Asn Phe Asp Cys
                20                  25                  30

Cys Leu Gly Tyr Thr Asp Arg Ile Leu His Pro Lys Phe Ile Val Gly
            35                  40                  45

Phe Thr Arg Gln Leu Ala Asn Glu Gly Cys Asp Ile Asn Ala Ile Ile
    50                  55                  60

Phe His Thr Lys Lys Lys Leu Ser Val Cys Ala Asn Pro Lys Gln Thr
65                  70                  75                  80

Trp Val Lys Tyr Ile Val Arg Leu Leu Ser Lys Lys Val Lys Asn Met
                85                  90                  95
```